United States Patent
Al-Shammari et al.

(10) Patent No.: US 10,005,858 B2
(45) Date of Patent: Jun. 26, 2018

(54) BORON-BRIDGED 2-INDENYL METALLOCENE COMPLEXES FOR OLEFIN POLYMERIZATION

(71) Applicant: SABIC GLOBAL TECHNOLOGIES B.V., Bergen Op Zoom (NL)

(72) Inventors: Haif Al-Shammari, Riyadh (SA); Yunshan Sun, Toronto (CA); Douglas Wade Stephan, Toronto (CA); Salah Al Hubish, Riyadh (SA); Zhu Jiangtao, Toronto (CA)

(73) Assignee: SABIC GLOBAL TECHNOLOGIES B.V., Bergen Op Zoom (NL)

( * ) Notice: Subject to any disclaimer, the term of this patent is extended or adjusted under 35 U.S.C. 154(b) by 0 days. days.

(21) Appl. No.: 15/509,309

(22) PCT Filed: Sep. 7, 2015

(86) PCT No.: PCT/EP2015/070335
§ 371 (c)(1),
(2) Date: Mar. 7, 2017

(87) PCT Pub. No.: WO2016/037960
PCT Pub. Date: Mar. 17, 2016

(65) Prior Publication Data
US 2017/0260304 A1 Sep. 14, 2017

Related U.S. Application Data

(60) Provisional application No. 62/212,626, filed on Sep. 1, 2015.

(30) Foreign Application Priority Data

Sep. 10, 2014 (EP) .................................... 14184193
Oct. 9, 2014 (EP) .................................... 14188257

(51) Int. Cl.
*C07F 17/00* (2006.01)
*C08F 4/6592* (2006.01)
(Continued)

(52) U.S. Cl.
CPC ............ *C08F 110/02* (2013.01); *C07F 5/027* (2013.01); *C07F 17/00* (2013.01);
(Continued)

(58) Field of Classification Search
CPC C08F 4/65927; C08F 4/65912; C08F 210/16; C07F 17/00
See application file for complete search history.

(56) References Cited

U.S. PATENT DOCUMENTS 5,962,718 A 10/1999 Reetz et al.
6,284,905 B1 * 9/2001 Ashe, III ................ C07F 17/00
502/103

(Continued)

FOREIGN PATENT DOCUMENTS

DE 19539650 A1 4/1997
EP 1710247 A1 10/2006
EP 2113521 A1 11/2009

OTHER PUBLICATIONS

Ashe III, Arthur J., et al., "Aminoboranediyl-Bridged Zirconocenes: Highly Active Olefin Polymerization Catalysts", Organometallics, May 18, 1999, vol. 18, No. 12, pp. 2288-2290.
(Continued)

*Primary Examiner* — Caixia Lu
(74) *Attorney, Agent, or Firm* — Cantor Colburn LLP

(57) ABSTRACT

A metallocene complex I, II, III and IV, (I)

(II)

(III)

(Continued)

-continued (IV)

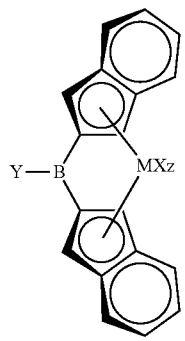

wherein

Y is a $C_1$-$C_{20}$ linear, branched or cyclic hydrocarbyl group, or a $C_6$-$C_{30}$ aryl or substituted aryl group;

L is an electron-donating ligand;

A is an element selected from Group 15 or 16;

R is a $C_1$-$C_{30}$ alkyl, aryl, or substituted aryl group;

n is an integer from 1 to 3;

m is an integer from 1 to 4;

B is a boron atom;

M is selected from lanthanides or transition metals from group 3, 4, 5 or 6;

X is an anionic ligand to M and z is the valence of M minus 2; and a catalyst comprising a 2-indenyl metallocene complex, a ligand precursor, a process for preparation of a ligand precursor, a process for preparation of olefin polymers in the presence of 2-indenyl metallocene complexes, articles comprising an olefin polymer, and methods of making the articles.

13 Claims, 1 Drawing Sheet

(51) Int. Cl.
  *C08F 210/16* (2006.01)
  *C08F 110/02* (2006.01)
  *C07F 5/02* (2006.01)

(52) U.S. Cl.
  CPC ........ *C08F 4/65927* (2013.01); *C08F 210/16* (2013.01); *C08F 2500/07* (2013.01)

(56) References Cited

U.S. PATENT DOCUMENTS

| | | | | |
|---|---|---|---|---|
| 2001/0025115 | A1* | 9/2001 | Campbell, Jr. | C07F 17/00 556/7 |
| 2003/0199650 | A1* | 10/2003 | Devore | C07F 17/00 526/160 |
| 2005/0176901 | A1* | 8/2005 | Arai | C08F 10/00 526/127 |

OTHER PUBLICATIONS

Braunschweig, Holger, et al., "Borametallocenophanes as catalysts for ethene polymerization", Zeitschrift fuer Anorganische und Allgemeine Chemie (2005), 631(13-14), pp. 2858-2866; Chemical Abstracts Service, Columbus, Ohio, 2005, retrieved from STN Database accession No. 2005:1215629.
International Search Report and Written Opinion for PCT/EP2015/070335 dated Feb. 5, 2016, 25 pages.
Reetz, Manfred T., et al., "Donor Complexes of BIS(1-indenyl) Phenylborane dischlorozirconium as isospecific catalysts in propene polymerization", Chem. Commun., 1999, pp. 1105-1106.
Crimmin et al. "Wittig-olefination via an yttrium-coordinated betaine", Chem. Commun. 2012, vol. 48, pp. 1745-1747.
Lewkebandara et al. Adducts of titanium tetrachloride with organosulfur compounds. Crystal and molecular structures of TiCl4(C4H8S)2 and (TiCl4)2(CH3SSCH3), Polyhedron, 1998, vol. 17, No. 1, pp. 1-9.
Peacock A. "Handbook of Polyethylene" Chapter 3, Marcel Dekker, Inc. ISBN: 0-8247-9546-6 (2000) pp. 43-66.
Randall et al. "A Review of High Resolution Liquid Carbon Nuclear Magnetic Resonance Characterizations of Ethylene-Based Polymers", Journal of Macromolecular Science—Reviews in Macromolecular Chem & Phys, C29 vol. 2 & 3, 1989, 16 pages.
Rudin A. "Measurement of Long-Chain Branch Frequency in Synthetic Polymers" Modern Methods of Polymer Characterization, Chapter 3, 1991, 12 pages.
Sassmannshausen Chemistry of Half-Sandwich Compounds of Zirconium: Evidence for the Formation of the Novel ansa Cationic-Zwitterionic Complex [Zr(n:n-C5H4CMe2C6H4Me-p)(u-MeB(CbF5)3)]+[MeB(C6F5)3], Organometallics, 2000, vol. 19, pp. 482-489.
Seenivasan et al. "Spectroscopic Investigation of Heterogeneous Ziegler-Natta Catalysts: Ti and Mg Chloride Tetrahydrofuranates, Their Interaction Compound, and the Role of the Activator", Chemistry—a European Journal, 2011, vol. 17, pp. 8648-8656.
Zimm et al. "The Dimensions of Chain Molecules Containing Branches and Rings," The Journal of Chemical Physics, vol. 17, No. 12 (Dec. 1949) pp. 1301-1314.

* cited by examiner

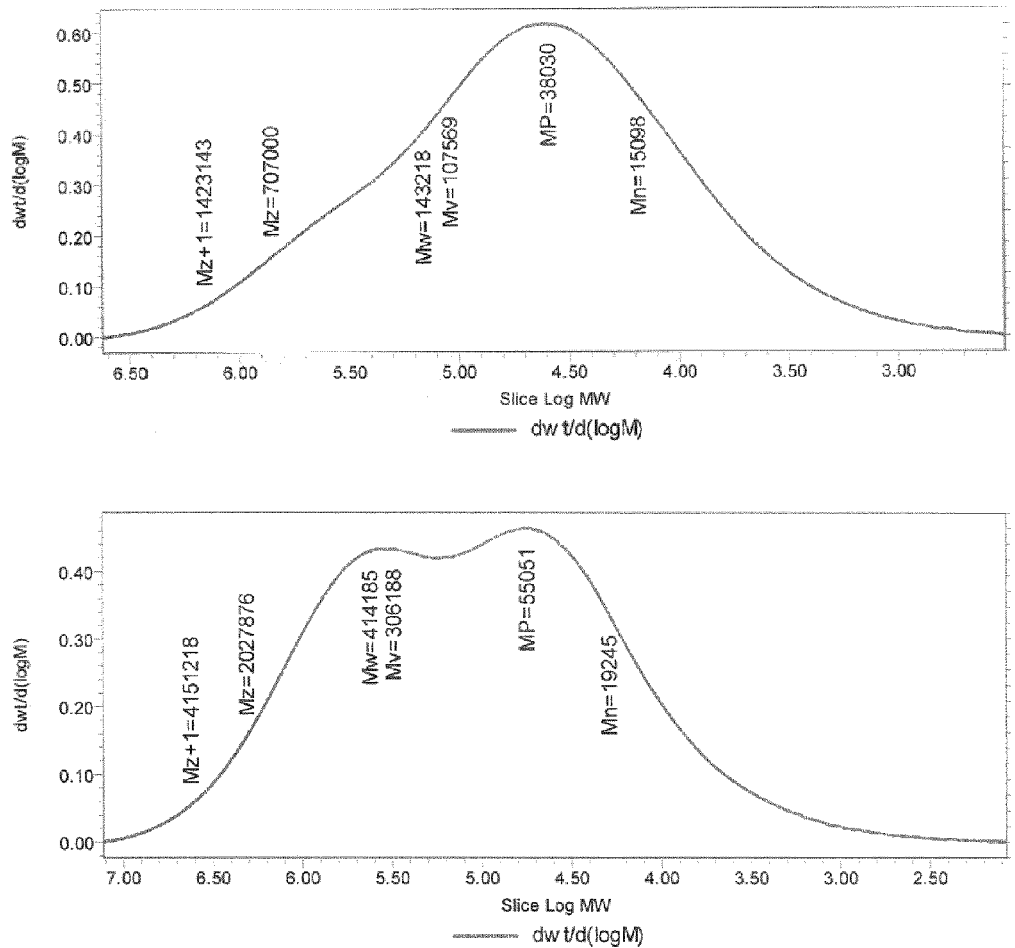
GPC spectra of the polyethylenes produced with compound 3 (top) and compound 4 (bottom).

BORON-BRIDGED 2-INDENYL METALLOCENE COMPLEXES FOR OLEFIN POLYMERIZATION

CROSS-REFERENCE TO RELATED APPLICATIONS

This application is a national stage application of PCT/EP2015/070335 filed Sep. 7, 2015, which claims priority to European Patent Application Number EP14184193.2 filed Sep. 10, 2014, European Patent Application Number EP14188257.1 filed Oct. 9, 2014, and U.S. Provisional Application No. 62/212,626 filed Sep. 1, 2015, all of which are hereby incorporated by reference in their entirety.

The invention relates to 2-indenyl metallocene complexes, a catalyst comprising a 2-indenyl metallocene complex, a ligand precursor, a process for the preparation of a ligand precursor, a process for the preparation of olefin polymers in the presence of 2-indenyl metallocene complexes, the use of the olefin polymers for making articles and articles comprising an olefin polymer.

Metallocene complexes together with a cocatalyst form catalysts that are widely used for olefin polymerization. The metallocene complexes are known to have only one active polymerization site and are often mentioned to be single site catalysts. The presence of one active site is believed to result in polymers having a narrow molecular weight distribution (MWD). An advantage of metallocene catalysts is their high activity and well defined structures compared to traditional Ziegler-Natta catalysts.

In contrast, Ziegler-Natta catalysts are known to contain plural catalytic sites. The Ziegler-Natta catalysts produce polymers having a broad MWD.

The use of single site catalysts for olefin polymerization reactions may have the disadvantage of producing olefin polymers having narrow molecular weight distributions (MWD) due to the identical active sites of the catalyst. This can cause problems for the industrial processing, like extrusion or injection moulding, of these olefin polymers. Polyolefins with broader MWD's are more easy to process. Polyolefins having a broader MWD are further desirable because these polyolefins combine the advantageous mechanical properties of the high molecular weight fraction, such as toughness, strength, and environmental stress cracking resistance, with the improved processing properties of the low molecular weight fraction.

Known methods for the production of polyolefins with broad molecular weight distributions are melt blending, producing polyolefins in a reactor in series configuration, or producing polyolefins in a single reactor with dual site catalysts. Melt blending suffers from the disadvantages brought on by the requirement of complete homogenization and high production costs. In addition, segregation of the blend components occurs due to the different properties of the components of the blend which makes it difficult to maintain a constant quality of the resulting products. The production of polyolefins in two reactors linked in series results is an expensive production method due to the costly process required. The production of polyolefins in a single reactor using dual site catalysts is widely employed. In addition to segregation of the different polyolefins, another problem of this method is to find common polymerization conditions where all catalysts show good activities. In most cases, the production of polyolefins with mixtures of two mononuclear catalysts leads to polyolefins with averaged molecular weights.

There is a need for a highly active catalyst, which is able to produce polyolefins in a high yield, wherein the polyolefins have a tunable molecular weight distribution (MWD) and a high molecular weight.

A new family of metallocene complexes has now been discovered which advantageously can be used for olefin polymerization, preferably for ethylene polymerization.

Metallocene Complexes

The invention relates to metallocene complexes which are selected from the group consisting of 2-indenyl complexes I, II, III and IV,

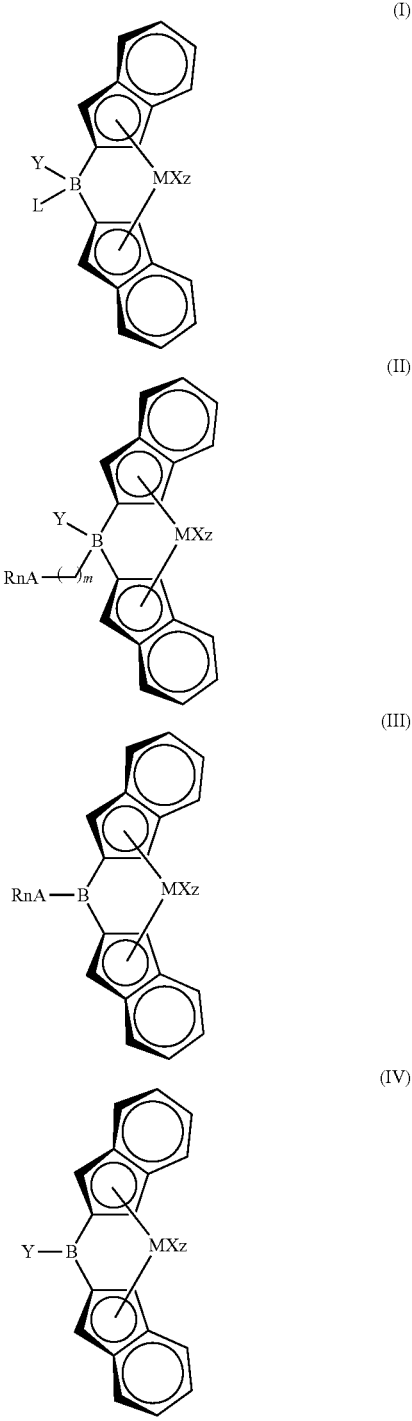

wherein

Y is a $C_1$-$C_{20}$ linear, branched or cyclic hydrocarbyl group, or a $C_6$-$C_{30}$ aryl or substituted aryl group;

L is an electron-donating ligand;

A is an element selected from Group 15 or 16 of the Periodic System of the Elements;

R is a $C_1$-$C_{30}$ alkyl, aryl, or substituted aryl group;

n is the number of R groups and is an integer from 1 to 3;

m is the number of carbon atoms in the hydrocarbyl group between A and B and is an integer from 1 to 4;

B is a boron atom;

M is a metal selected from lanthanides or transition metals from group 3, 4, 5 or 6 of the Periodic System of the Elements;

X is an anionic ligand to M and z is the number of X groups and equals the valence of M minus 2.

It has surprisingly been discovered that the metallocene complexes according to the invention form part of single site metallocene catalysts, that can produce monomodal, bimodal and multimodal molecular weight distributions (MWD). A further advantage of the metallocene complexes according to the invention is that these complexes can produce polyethylenes with high molecular weights. The metallocene complexes allow a broad variation of polyolefin properties because small changes in the catalyst structure can cause great changes in the polyolefin properties.

In the metallocene complexes according to the invention Y is a $C_1$-$C_{20}$ linear, branched or cyclic hydrocarbyl group, or a $C_6$-$C_{30}$ aryl or substituted aryl group. Examples of linear $C_1$-$C_{20}$ hydrocarbyl groups are methyl, ethyl, n-butyl, n-octyl and n-octadecyl groups. Examples of branched $C_1$-$C_{20}$ hydrocarbyl groups are 2-propyl, t-butyl, iso-pentyl and 1,1-dimethylhexyl. Examples of cyclic $C_1$-$C_{20}$ hydrocarbyl groups are cyclopropyl, cyclohexyl and cyclopentenyl. Examples of $C_6$-$C_{30}$ aryl groups are phenyl, mesityl, tolyl, cumenyl, benzyl, pentamethylbenzyl, naphthyl, xylyl, styryl and trityl. Preferably, Y is a $C_6$-$C_{30}$ aryl group or substituted aryl group, more preferably phenyl or a substituted phenyl group.

In the metallocene complexes according to the invention L is an electron-donating ligand. Electron donating ligands are ligands that bind to an atom by electrostatic interactions, but do not form a covalent bond with this atom. Preferably, the electron-donating element in the ligand L is an element from group 15 or 16 of the Periodic System of the Elements. The Periodic System of the Elements is understood to be the Periodic System of the Elements that can be found at www.chemicool.com.

Examples of suitable ligands L are a nitro group, a nitroso group, an alkyloxy group, a thioalkyl group, a hydroxy group, aldehydes, acids, sulfuric acids, anhydrides, esters, peroxides, furans, amines, amides, imides, pyridines, sulfides and phosphines. Preferred examples of ligands L are pyridines, tetrahydrofuran, dialkylsulfide and trialkylphosphines. Most preferred examples of L are pyridine, tetrahydrofuran, dimethylsulfide and trimethylphosphine.

In the metallocene complexes according to the invention A is an element selected from Group 15 or 16 of the Periodic System of the Elements, preferably A is selected from the group of O, S, N and P.

In the metallocene complexes according to the invention R is a $C_1$-$C_{30}$ alkyl, aryl, or substituted aryl group. Examples of $C_1$-$C_{30}$ alkyl groups are methyl, ethyl, propyl, n-butyl, 2-octyl and 5-octadecyl groups. Examples of aryl groups are phenyl, indenyl, naphthyl and biphenyl. Examples of substituted aryl groups are cumenyl, pentamethylbenzyl, xylyl, tolyl and mesityl.

Preferred examples of $AR_n$ are trialkylphosphides, dialkylamides, trialkylamides, dialkylsulphides, alkoxy groups and aryloxy groups, for example trimethylphosphide, dimethylamide, diethylamide, dimethylsulphide, diisopropylamide, isopropoxy, t-butoxy and phenoxy.

In the metallocene complexes according to the invention n is the number of R groups and is an integer from 1 to 3. Preferably, n is 2 or 3.

In the metallocene complexes according to the invention m is the number of carbon atoms in the hydrocarbyl group between A and B and is an integer from 1 to 4; preferably m is 1 or 2.

The metallocene complexes according to the invention comprise a metal (M) selected from lanthanides or transition metals from group 3, 4, 5 or 6 of the Periodic System of the Elements. The metal M is preferably chosen from the group consisting of Ti, Zr, Hf, V and Sm, more preferably from Ti, Zr and Hf, most preferably the metal is Zr.

X is an anionic ligand to M. The X ligand preferably is selected from the group consisting of halogen (F, Cl, Br, I) and hydrocarbyl groups comprising 1 to 20 carbon atoms. More preferably the X ligand is Cl or a methyl group. In case more than one X ligand is present, the ligands can be the same or different. Preferably, the X ligands are the same.

z is the number of X groups and equals the valence of M minus 2; z is an integer. Preferably, z is 2.

Preferred Metallocene Complex

A preferred metallocene complex is a 2-indenyl metallocene complex according to formula I wherein Y is a phenyl group;

A is O, S, N or P;

R is a $C_1$-$C_{30}$ alkyl, aryl, or substituted aryl group and n is the number of R groups and is an integer from 1 to 3;

B is a boron atom;

M is chosen from the group consisting of Ti, Zr and Hf;

X is Cl or a methyl group and z is the number of X groups and equals the valence of M minus 2.

Support

The metallocene complex can be immobilized on a support. The support is preferably an inert support, more preferably a porous inert support. Examples of porous inert supports materials are talc and inorganic oxides. Preferably, the support material is in a finely divided form.

Suitable inorganic oxide materials include group 2A, 3A, 4A and 4B metal oxides such as silica, alumina and mixtures thereof. Other inorganic oxides that may be employed either alone or in combination with the silica or alumina are magnesia, titania, zirconia and the like. Other support materials, however, can be employed, for example finely divided functionalized polyolefins such as finely divided polyethylene.

Preferably, the support is a silica having a surface area between 200 and 900 $m^2$/g and a pore volume between 0.5 and 4 ml/g.

Catalyst

The invention is also directed to a catalyst prepared from the metallocene complex according to the invention and a cocatalyst. The cocatalyst includes aluminium- or boron-containing cocatalysts. Suitable aluminium-containing cocatalysts comprise aluminoxanes and alkyl aluminium. The aluminoxanes usable according to the present invention are well known and preferably comprise oligomeric linear and/or cyclic alkyl aluminoxanes represented by the formula: $R^3$—$(AlR^3$—$O)_n$—$AlR^3{}_2$ for oligomeric, linear aluminoxanes and $(—AlR^3—O—)_m$ for oligomeric, cyclic aluminoxanes; wherein n is 1-40, preferably n is 10-20; m is 3-40, preferably m is 3-20 and $R^3$ is a $C_1$ to $C_8$ alkyl group and preferably a methyl group. Further other organoaluminum compounds can be used such as trimethylaluminum, triethylaluminium, triisopropylaluminum, tri-n-propylaluminum, triisobutylaluminum, tri-n-butylaluminum, triamylaluminium; dimethylaluminium ethoxide, diethylaluminium ethoxide, diisopropylaluminium ethoxide, di-n-propylaluminium ethoxide, diisobutylaluminium ethoxide and di-n-butylaluminium ethoxide; dimethylaluminium hydride, diethylaluminium hydride, diisopropylaluminium hydride, di-n-propylaluminium hydride, diisobutylaluminium hydride and di-n-butylaluminium hydride.

Suitable boron-containing cocatalysts include trialkylboranes, for example trimethylborane or triethylborane and/or perfluorophenylborane and/or a perfluorophenylborate.

In the process to produce olefin polymers by polymerizing one or more olefins in the presence of a metallocene complex preferably an organoaluminum cocatalyst is present.

More preferably, methylaluminoxane is used as the cocatalyst.

Ligand Precursor and Preparation of the Ligand Precursor

The invention is also directed to a ligand precursor selected from the group consisting of ligand precursors according to formula V or VI,

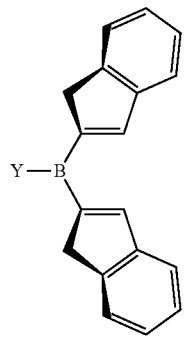

(V)

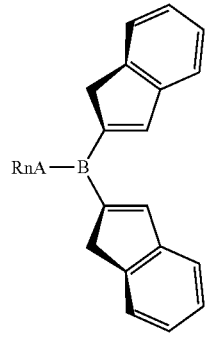

(VI)

wherein,
Y is a $C_1$-$C_{20}$ linear, branched or cyclic hydrocarbyl group, or a $C_6$-$C_{30}$ aryl or a substituted aryl group;
A is an element selected from Group 15 or 16 of the Periodic System of the Elements;
R is a $C_1$-$C_{30}$ alkyl, aryl, or substituted aryl group;
n is the number of R groups and is an integer from 1 to 3; and
B is a boron atom;
with the exception of bis(2-indenyl)(diisopropylamino) borane.

The compound bis(2-indenyl)(diisopropylamino)borane is described in the patent publications EP2113521 and in EP1710247 as an intermediate compound that is used in the preparation of double bridged metallocene complexes. In these complexes a boron-containing bridge and a silicium-containing bridge are both present between the two cyclopentadienyl groups in the ligand. In both patent publications metallocene complexes comprising a bis (2-indenyl)(diisopropylamino)borane ligand have not been disclosed.

The invention is further directed to a process for the preparation of a ligand precursor of formula V or VI comprising the steps of
  a. Activating Mg with 1,2-dibromoethane,
  b. Reacting the activated Mg with 2-bromoindene to form a Grignard solution
  c. Reacting the Grignard solution with $Me_3SnCl$ to form a compound according to formula VII and

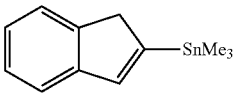

(VII)

d. Reacting the compound according to formula VII with dichloroYB or dichloro($R_nA$)B, to form the ligand precursor according to formula V or VI, wherein Y is a $C_1$-$C_{20}$ linear, branched or cyclic hydrocarbyl group, or a $C_6$-$C_{30}$ aryl or substituted aryl group; A is an element selected from Group 15 or 16 of the Periodic System of the Elements; R is a $C_1$-$C_{30}$ alkyl, aryl, or substituted aryl group; n is the number of R groups and is an integer from 1 to 3; and B is a boron atom.

Olefin Polymerization

In another aspect, the invention relates to a process for the preparation of olefin polymers by polymerizing one or more olefins in the presence of a cocatalyst and the metallocene complex of the invention, wherein the metallocene complex optionally is immobilized on a support.

The process to produce the olefin polymers may start with the reaction of the metallocene complex according to the invention with the cocatalyst. This reaction can be performed in the same vessel as the reaction vessel wherein the olefin polymers are produced or in a separate vessel, whereafter the mixture of the metallocene complex and the cocatalyst is fed to the reaction vessel. During the reaction described above an inert solvent can be used.

In the mixture of the metallocene complex and the cocatalyst, the cocatalyst is used in an amount of 10 to 100,000 mol, preferably from 10 to 10,000 mol per mol of the transition metal compound.

The solvent used in the process to produce olefin polymers may be any organic solvent usually used for the polymerization. Examples of solvents are benzene, toluene, xylene, butane, pentane, hexane, heptane, cyclohexane and methylene chloride. Also the olefin to be polymerized can be used as the solvent.

In the process to produce olefin polymers the polymerization conditions, like for example temperature, time, pressure, monomer concentration can be chosen within wide limits. The polymerization temperature is in the range from −100 to 300° C., preferably 0 to 200° C., more preferably 10 to 100° C. The polymerization time is in the range of from 10 seconds to 20 hours, preferably from 1 minute to 10 hours, more preferably from 5 minutes to 5 hours. The ethylene pressure during polymerization is in the range from 1 to 3500 bar, preferably from 1 to 2500 bar, more preferably from 1 to 1000 bar, even more preferably from 1 to 500 bar, most preferably from 1 to 100 bar. The molecular weight of the polymer can be controlled by use of hydrogen in the polymerization. The polymerization may be conducted by a batch process, a semi-continuous process or a continuous process and may also be conducted in two or more steps of different polymerization conditions. The polyolefin produced is separated from the polymerization solvent and dried by methods known to a person skilled in the art.

In the process to produce olefin polymers the olefin which is polymerized can be one type of olefin or can be mixtures of different olefins. The polymerization thus includes homopolymerization and copolymerization. Examples of olefins are α-olefins such as ethylene, propylene, 1-butene, 1-pentene, 4-methyl-1-pentene, 1-hexene, 1-octene, 1-nonene, 1-decene and styrene; conjugated and non-conjugated dienes such as butadiene, 1,4-hexadiene, 5-ethylidene-2-norbornene, dicyclopentadiene, 4-methyl-1,4-hexadiene and 7-methyl-1,6-octadiene; and cyclic olefins such as cyclobutene, but is not limited thereto.

Preferably, at least one of the olefins that is polymerized is ethylene. More preferably, a mixture of ethylene and at least one other α-olefin of 3 or more carbon atoms is polymerized.

Preferably, the other olefin of 3 or more carbon atoms is chosen from 1-butene, 1-hexene or 1-octene, more preferably the other olefin is 1-hexene.

Preferably, the olefin comonomer is present in an amount of about 5 to about 20 percent by weight of the ethylene-olefin copolymer, more preferably an amount of from about 7 to about 15 percent by weight of the ethylene α-olefin copolymer.

For example a linear low density polyethylene (LLDPE) having a melt mass flow rate (also known as melt flow index) as determined using ASTM D1238-10 (190° C./2.16 kg) which ranges from 1 to 125 g/10 min and a density in the range from 900 kg/m$^3$ to less than 940 kg/m$^3$ as determined using ASTM D1505-10 may be obtained. For example, the density of the LLDPE ranges from about 915 kg/m$^3$ to less than 940 kg/m$^3$, for example between 915 and 925 kg/m$^3$. For example, the melt flow index of the LLDPE ranges from 0.3 to 3 g/10 min, for example from 0.5 to 1.5 g/10 min.

The polymerisation may be performed via a gas phase process or via a slurry process. The production processes of polyethylene are summarised in "Handbook of Polyethylene" by Andrew Peacock (2000; Dekker; ISBN 0824795466) at pages 43-66.

The various processes may be divided into solution polymerisation processes employing homogeneous (soluble) catalysts and processes employing supported (heterogeneous) catalysts. The latter processes include both slurry and gas phase processes.

The invention is also directed to a polyolefin, for example polyethylene, preferably high density polyethylene (HDPE) obtainable or obtained by the process of the invention, for example by copolymerizing ethylene and at least one other olefin in the presence of a metallocene complex according to the invention or a composition, wherein the metallocene complex according to the invention is immobilized on a support.

As defined herein, in linear low density polyethylene, the term "linear" means that the polymer lacks measurable or demonstrable long chain branches, that is, the polymer is substituted with an average of less than 0.01 long chain branch/1000 carbon atoms.

"Long chain branching" (LCB) means a chain length longer than the short chain branch that results from the incorporation of the α-olefin(s) into the polymer backbone. Each long chain branch will have the same comonomer distribution as the polymer backbones and can be as long as the polymer backbone to which it is attached.

As a practical matter, current $^{13}$C nuclear magnetic resonance spectroscopy cannot distinguish the length of a long chain branch in excess of six carbon atoms. However, there are other known techniques useful for determining the presence of long chain branches in ethylene polymers. Two such methods are gel permeation chromatography coupled with a low angle laser light scattering detector (GPC-LALLS) and gel permeation chromatography coupled with a differential viscometer detector (GPCDV). The use of these techniques for long chain branch detection and the underlying theories have been well documented in the literature.

See, for example, Zimm, G. H. and Stockmayer, W. H., J. Chem. Phys., 17,1301 (1949) and Rudin, A., Modern Methods of Polymer Characterization, John Wiley & Sons, New York (1991 pp. 103-112).

It has been found that with the metallocene complex of the invention or with the composition of the invention wherein the metallocene complex of the invention is present on a support, it is possible to produce polyethylene from ethylene and at least one other olefin, for example an olefin having up to 8 carbon atoms, with a high incorporation of the at least one other olefin.

The amount of incorporation of the at least one other olefin, for example an α-olefin in the polyethylene is expressed by the amount of branches per 1000 carbon atoms.

The presence of short chain branching of up to 6 carbon atoms in length can be determined in ethylene polymers by using $^{13}$C nuclear magnetic resonance (NMR) spectroscopy and is quantified using the method described by Randall (Rev. Macromol. Chem. Phys., C. 29, V. 2 & 3, p. 285-297).

Therefore, the invention also relates to a polyolefin, preferably polyethylene, for example linear low density polyethylene (LLDPE). The low density polyethylene, for example LLDPE, preferably has an amount of branches per 1000 carbon atoms as determined using $^{13}$C NMR of at least 18, for example of at least 19, for example at least 20 and/or for example at most 30, for example at most 25, for example at most 23, for example at most 21. Preferably, said polyethylene is substituted with an average of less than 0.01 long chain branch per 1000 carbon atoms.

The number average molecular weight (Mn) of the polyolefin, for example polyethylene, for example LLDPE of the invention may vary between wide ranges and may for example be in the range from 1000 to 200000 Da.

For example, the Mn of the polyolefin of the invention may be at least 1500, for example at least 2000, for example at least 20,000, for example at least 50,000 and/or for example at most 150,000, for example at most 110,000, for example at most 100,000, for example at most 70,000 Da.

The weight average molecular weight (Mw) of the polyolefin, for example polyethylene, for example LLDPE of the invention may also vary between wide ranges and may for example be in the range from 1500 to 500000. For example, the Mw of the polyolefin of the invention may be at least 2500, for example at least 10,000, for example at least 50,000, for example at least 100,000 and/or for example at most 400,000, for example at least 350,000, for example at most 300,000, for example at most 250,000.

For purpose of the invention, the Mw and Mn are determined using SEC (Size Exclusion Chromatography) using 1,2,4-trichlorobenzene as an eluent, and calibrated using linear polyethylene standards.

The molecular weight distribution (that is Mw/Mn) of the polyolefin of the invention may for example vary from 2 to 5, from 2.1 to 4 or from 2.5 to 3.5.

The crystallinity temperature ($T_a$) of the polyolefin of the invention may for example be in the range from 90 to 120° C. The melt temperature ($T_m$) of the polyolefin of the invention may for example be in the range from 100 to 140° C.

For purpose of the invention, the $T_m$ and $T_c$ are determined using Differential Scanning calorimetry according to ASTM D 3418-08 using a scan rate of 10° C./min on a sample of 10 mg and using the second heating cycle The polyolefin obtained or obtainable by the process of the invention may be mixed with suitable additives.

Examples of suitable additives for polyethylene include but are not limited to the additives usually used for polyethylene, for example antioxidants, nucleating agents, acid scavengers, processing aids, lubricants, surfactants, blowing agents, ultraviolet light absorbers, quenchers, antistatic agents, slip agents, anti-blocking agents, antifogging agents, pigments, dyes and fillers, and cure agents such as peroxides. The additives may be present in the typically effective amounts well known in the art, such as 0.001 weight % to 10 weight % based on the total composition.

The polyolefins of the invention and compositions comprising said polyolefins may suitably be used for the manufacture of articles. For example, the polyolefins and compositions of the invention may be manufactured into film, for example by compounding, extrusion, film blowing or casting or other methods of film formation to achieve, for example uniaxial or biaxial orientation. Examples of films include blown or cast films formed by coextrusion (to form multilayer films) or by lamination and may be useful as films for packaging, for example as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets.

Therefore, in another aspect, the invention also relates to articles comprising the polyolefins obtainable by the process of the invention.

In yet another aspect, the invention also relates to use of the polyolefins obtainable by the process of the invention for the preparation of articles, for example for the preparation of films.

In yet another aspect, the invention relates to a process for the preparation of articles using the polyolefin according to the invention.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will hereafter be elucidated by way of the following examples, without being limited thereto.

FIGURE

FIG. 1 shows GPC data of polyethylenes prepared with two different catalysts according to the invention. The top diagram shows the GPC spectrum of the polyethylene produced with a catalyst comprising compound 3 (top) and while the bottom diagram shows the GPC spectrum of the polyethylene produced with compound 4 (bottom).

EXAMPLES

General Considerations

All manipulations were carried out under an atmosphere of dry, $O_2$-free $N_2$ employing an Innovative Technology glove box and a Schlenk vacuum-line. Tetrahydrofuran (THF), toluene, methylene chloride, hexane and pentane were purified with a Grubbs-type column system manufactured by Innovative Technology and dispensed into thick-walled Schlenk glass flasks equipped with Teflon-valve stopcocks. Pyridine was dried over the appropriate agents and distilled into the same kind of storage flasks. Anhydrous benzene (Alfa, 99.8%, packaged under argon) was purchased and used as received. Deuterated solvents were dried over the appropriate agents, vacuum-transferred into storage flasks with Teflon stopcocks and degassed accordingly ($CDCl_3$, $C_6D_6$ and $CD_2Cl_2$). $^1H$, $^{11}B$, $^{13}C$ and $^{31}P$ NMR spectra were recorded at 25° C. Bruker 400 MHz spectrometers. Chemical shifts are given relative to $SiMe_4$ and referenced to the residue solvent signal ($^1H$, $^{13}C$). $^{11}B$ and $^{31}P$ resonances were referenced externally to ($BF_3.Et_2O$) and 85% $H_3PO_4$, respectively. Chemical shifts are reported in ppm and coupling constants as scalar values in Hz. $ZrCl_4(Me_2S)_2$, $^1TiCl_4(THF)_2$,$^2$ and $TiCl_4(Me_2S)_2$,$^3$ were prepared as reported in, respectively, Sassmannshausen, J. *Organometallics* 2000, 19, 482-489; Seenivasan, K.; Sommazzi, A.; Bonino, F.; Bordiga, S.; Groppo, E. *Chemistry—a European Journal* 2011, 17, 8648-8656 and Suren Lewkebandara, T.; McKarns, P. J.; Haggerty, B. S.; Yap, G. P. A.; Rheingold, A. L.; Winter, C. H. *Polyhedron* 1998, 17, 1-9. $ZrCl_4(THF)_2$ (Strem) was purchased and used as received.

Example 1. Synthesis of trimethyl(1H-inden-2-yl)stannane

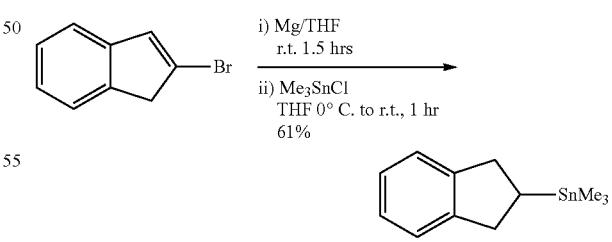

A Schlenk flask was charged with a magnetic stir bar and Mg turnings (1.85 g, 77 mmol, 3.0 eq.) and flame-dried under vacuum. After cooling, the flask was purged to $N_2$, anhydrous THF (15 mL) was added to just cover the turnings, and stirring was commenced. 1,2-dibromoethane (0.1 mL) was added as initiator, and a heat gun used to briefly reflux the contents, after which the flask was placed in a 25° C. water bath. In a separate flame-dried flask under N₂ atmosphere, 2-bromoindene (5.0 g, 25.6 mmol, 1.0 eq.) was dissolved in 25 mL anhydrous THF. A cannula was then used to transfer this solution onto the activated magnesium turnings over 10 min, resulting in a red, opaque solution. After 1.5 h, GCMS analysis of an aliquot sample showed consumption of the 2-bromoindene. A separate flame-dried flask under N₂ atmosphere was charged with Me₃SnCl (28.2 mL, 1.0M in hexane, 28.2 mmol, 1.1 eq.) in 15 mL anhydrous THF and cooled to 0° C. To this was added, by cannula, the Grignard solution over 10 min., and the reaction flask was brought to ambient temperature for an additional 1 hour. The mixture was quenched with chilled, saturated aq. NH₄Cl and Et₂O (60 mL) was added. The organic phase was separated and the aqueous layer was extracted with Et₂O (20 mL×1). The combined organic layers were washed with brine (20 mL×1), dried with anhydrous MgSO₄, filtered, and concentrated to an orange oil. This was pushed through a plug of activated, neutral alumina using hexanes, to provide, after removal of volatiles, the crude stannane reagent as a brown oil, which was purified via vacuum distillation to give pure trimethyl(1H-inden-2-yl)stannane (4.35 g, 61%) as a yellow oil. $^1$H-NMR (400 MHz, CDCl₃) δ 7.53 (1H, dd, J=0.8, 7.6 Hz), 7.44 (1H, d, J=7.6 Hz), 7.31 (1H, t, J=7.2 Hz), 7.20 (1H, td, J=7.2, 1.2 Hz), 7.13 (1H, td, J=2.0, 0.8 Hz), 3.53 (2H, d, J=2.0 Hz), 0.32 (9H, s). $^{13}$C-NMR (100 MHz, CDCl₃) δ 150.27, 147.06, 145.53, 141.66, 126.28, 124.26, 123.45, 120.22, 45.15, −9.50. ESI-HRMS (mz) calcd for $C_{12}H_{20}N^{120}Sn$ [M+NH₄⁺] 298.06177, found 298.06196.

Example 2. Synthesis of Compound 1

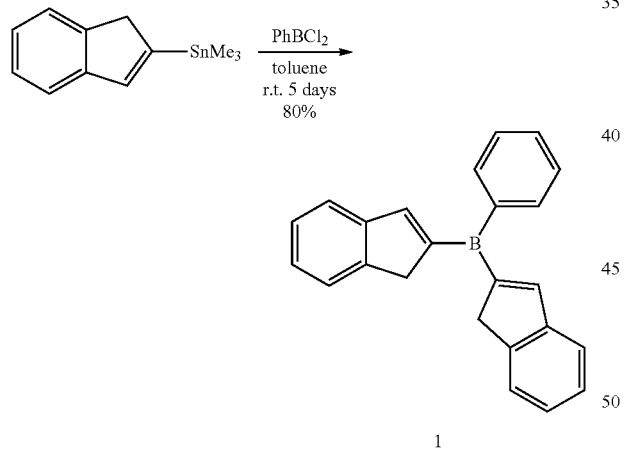

To a stirred solution of trimethyl(1H-inden-2-yl)stannane (7.16 g, 25.7 mmol, 2.2 eq.) in toluene (10 mL) was added a solution of dichlorophenylborane (2 g, 12.6 mmol, 1.0 eq.) in toluene (5 mL) dropwise at room temperature. The resulting yellow solution was then stirred at room temperature for 5 days. The solution was concentrated and the resulting solid was collected by filtration, washed with cold pentane (20 mL), dried in vacuo to give compound 1 (2.92 g, 73%) as a white powder. The filtrate was concentrated and the resulting solid was collected by filtration, washed with cold pentane (6 mL), dried in vacuo to give the second batch of compound 1 (0.3 g, 7%) as a white powder. $^{11}$B NMR (128 MHz, C₆D₆) δ 57.8; $^1$H-NMR (400 MHz, C₆D₆) δ 7.60-7.70 (4H, m), 7.26-7.48 (7H, m), 7.20-7.25 (4H, m), 3.63 (4H, s). $^{13}$C-NMR (100 MHz, C₆D₆) δ 153.21, 149.19, 145.45, 134.88, 129.50, 127.67, 127.26, 126.92, 124.37, 123.37, 43.97.

Example 3. Synthesis of Compound 2

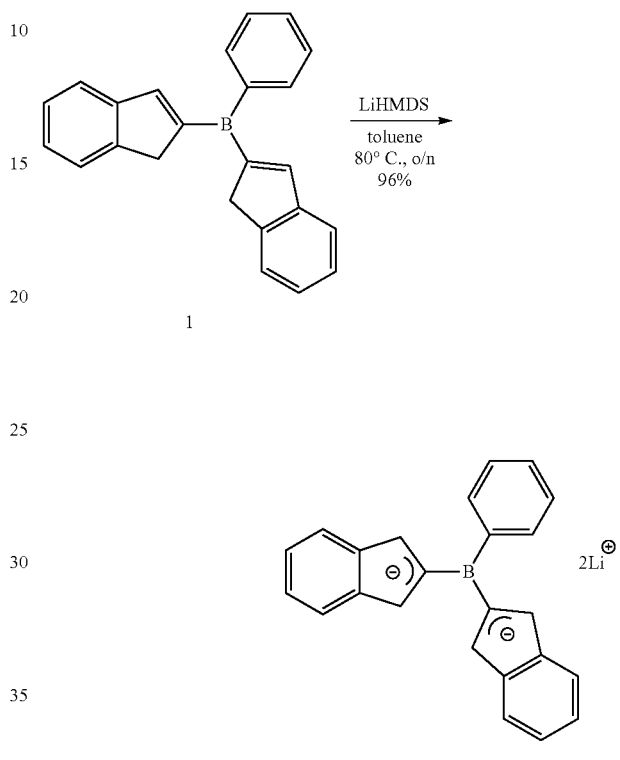

To a stirred solution of compound 1 (1.04 g, 3.27 mmol) in toluene (40 mL) was added LiHMDS (1.2 g, 7.17 mmol, 2.2 eq.) in one portion at room temperature. The resulting yellow solution was then stirred at 80° C. overnight to give a yellow suspension. The suspension was filtered, and the residue was washed with toluene (5 mL) and pentane (10 mL), then dried in vacuo to give compound 2 (1.04 g, 96%) as a yellow powder.

Example 4. Synthesis of Compound 3

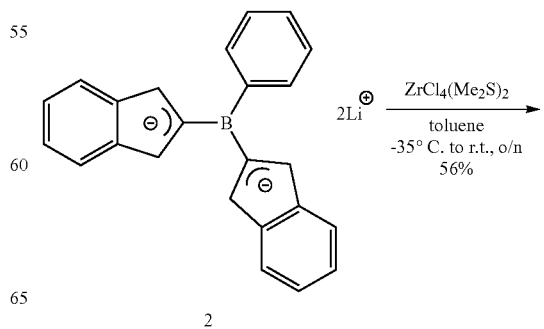

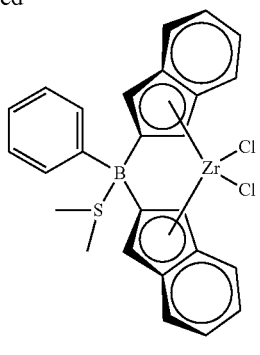

3

Method A:

To the pre-cooled (−35° C.) suspension of compound 2 (0.22 g, 0.67 mmol) in toluene (6 mL) was added ZrCl$_4$(Me$_2$S)$_2$ (0.25 g, 7.00 mmol, 1.05 eq.) in one portion. The resulting suspension was then stirred at room temperature for 5 days.

The mixture was filtered through celite and the residue was washed with toluene (5 mL). The combined filtrates were then discarded. The remaining solids were filtered through using methylene chloride (15 mL), which after concentration provided compound 3 (0.2 g, 56%) as a yellow powder. $^{11}$B NMR (128 MHz, CD$_2$Cl$_2$) δ −0.9; $^1$H NMR (400 MHz, CD$_2$Cl$_2$) δ 7.77 (2H, d, J=6.4 Hz), 7.45-7.51 (7H, m), 7.12-7.20 (4H, m), 6.34 (2H, d, J=2 Hz), 5.96 (2H, d, J=2 Hz), 2.18 (6H, s).

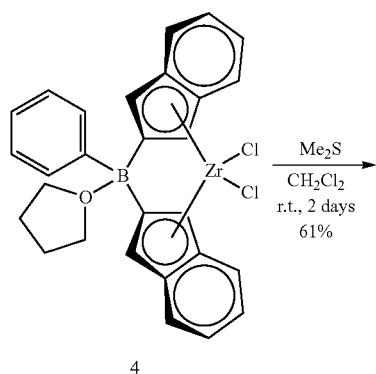

4

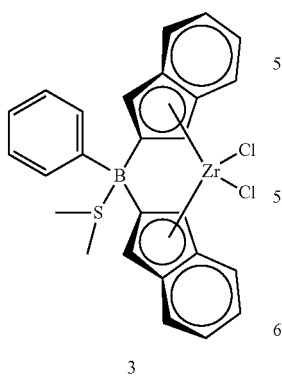

3

Method B:

To a stirred mixture of compound 4 (0.15 g, 0.27 mmol) in methylene chloride (3 mL) was added dimethyl sulfide (0.25 mL, 3.4 mmol, 12.6 eq.) at room temperature. The resulting yellow mixture was stirred at room temperature for 2 days. The mixture was concentrated in vacuo. Prior to the complete removal of the solvent, excess amount of hexane was added. The powder was collected by filtration and washed with hexane (6 mL×2), dried under high vacuum to give compound 3 (90 mg, 61%) as a yellow powder.

Example 5. Synthesis of Compound 4

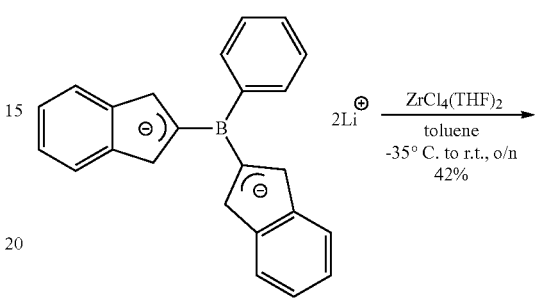

2

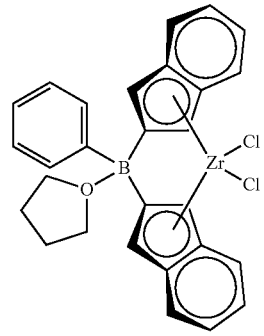

4

In the same manner (method A) as 3, compound 4 was synthesized as a yellow powder (0.14 g, 42%) from compound 2 (0.2 g, 0.60 mmol) and ZrCl$_4$(THF)$_2$ (0.23 g, 0.60 mmol, 1.0 eq.) in toluene (6 mL). Crystals suitable for X-ray diffraction were grown by vial-in-vial solvent diffusion of a concentrated solution of 4 in methylene chloride with hexanes. $^{11}$B NMR (128 MHz, CD$_2$Cl$_2$) δ 9.4; $^1$H NMR (400 MHz, CD$_2$Cl$_2$) δ 7.91 (2H, dd, J=2.0, 7.6 Hz), 7.46-7.51 (7H, m), 7.11-7.20 (4H, m), 6.28 (2H, d, J=1.6 Hz), 5.81 (2H, d, J=1.6 Hz), 4.58 (4H, s), 2.03 (4H, s).

Example 6. Synthesis of Compound 5

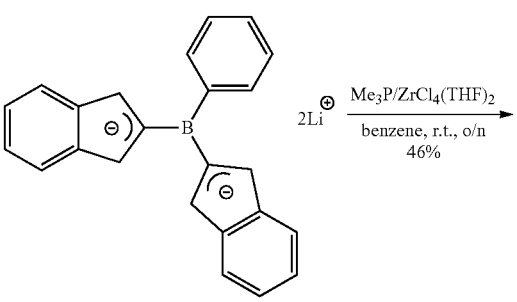

2

-continued

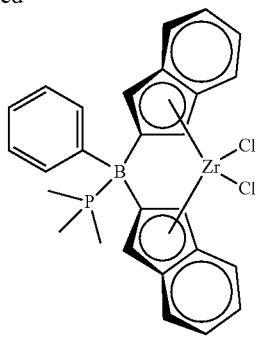

5

Method A:

To a stirred suspension of compound 2 (0.22 g, 0.67 mmol) in benzene (10 mL) was added trimethylphosphine (6 mL, 1.0M in toluene, 6 mmol, 9.0 eq.) at room temperature. The resulting red brown suspension was stirred at room temperature for 30 minutes before ZrCl$_4$(THF)$_2$ (0.26 g, 0.69 mmol, 1.03 eq.) was added in one portion at room temperature. After the suspension was stirred at room temperature for 5 days, it was filtered through celite and the residue was washed with benzene (6 mL). The combined filtrates were then discarded. The remaining solids were filtered through using methylene chloride (20 mL), which after concentration provided compound 5 (0.17 g, 46%) as a bright yellow powder. $^{11}$B NMR (128 MHz, CD$_2$Cl$_2$) δ −11.7 (m); $^{31}$P NMR (162 MHz, CD$_2$Cl$_2$) δ-15.4 (m); $^1$H NMR (400 MHz, CD$_2$Cl$_2$) δ 7.76-7.78 (2H, m), 7.49 (2H, d, J=8.4 Hz), 7.42 (4H, t, J=8.0 Hz), 7.33-7.37 (1H, m), 7.10-7.17 (4H, m), 6.14 (2H, d, J=2.4 Hz), 6.05 (2H, d, J=2.4 Hz), 1.55 (9H, d, J=10.4 Hz).

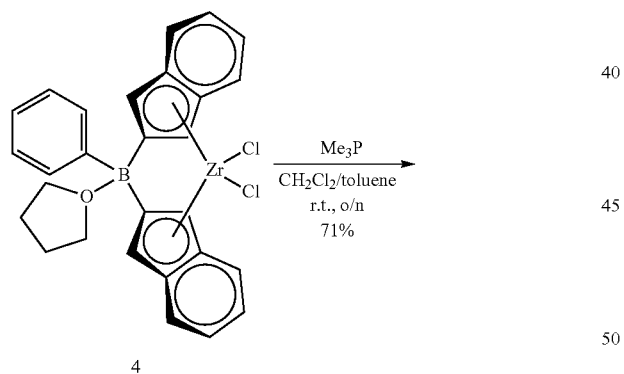

4

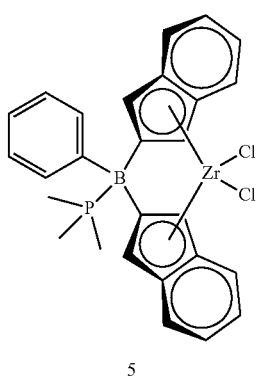

5

Method B:

To a stirred mixture of compound 4 (0.15 g, 0.27 mmol) in methylene chloride (3 mL) was added a solution of trimethylphosphine (1.5 mL, 1.0 M in toluene, 1.5 mmol, 5.6 eq.) at room temperature. The resulting yellow mixture was stirred at room temperature for overnight. The mixture was concentrated in vacuo. Prior to the complete removal of the solvent, excess amount of hexane was added. The powder was collected by filtration and washed with hexane (6 mL×2), dried under high vacuum to give compound 5 (0.11 g, 71%) as a yellow powder.

Example 7. Synthesis of Compound 6

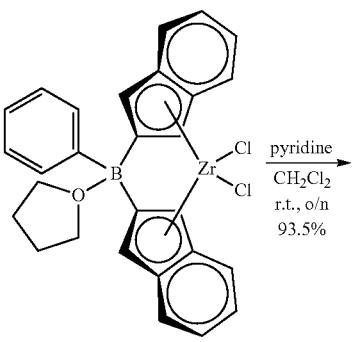

4

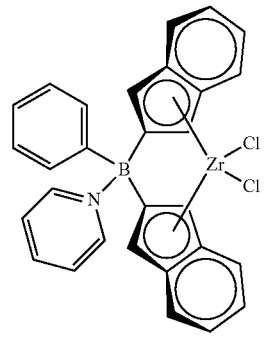

6

To a stirred yellow mixture of compound 4 (0.19 g, 0.35 mmol) in methylene chloride (8 mL) was added pyridine (31 uL, 0.38 mmol, 1.1 eq.) at room temperature. The resulting yellow mixture was stirred at room temperature for overnight. The mixture was concentrated in vacuo, washed with hexane (6 mL×2), dried under high vacuum to give compound 6 (0.18 g, 93.5%) as a bright yellow powder. $^{11}$B NMR (128 MHz, CD$_2$Cl$_2$) δ 1.4; $^1$H NMR (400 MHz, CD$_2$Cl$_2$) δ 9.34 (2H, dd, J=1.6, 6.8 Hz), 8.22 (1H, tt, J=1.6, 7.6 Hz), 7.93 (2H, dd, J=1.2, 8.0 Hz), 7.81 (2H, t, J=7.6 Hz), 7.43-7.52 (4H, m), 7.26-7.38 (3H, m), 7.12-7.20 (4H, m), 6.08 (2H, d, J=2.4 Hz), 5.92 (2H, d, J=2.4 Hz).

Example 8. Synthesis of Compound 7

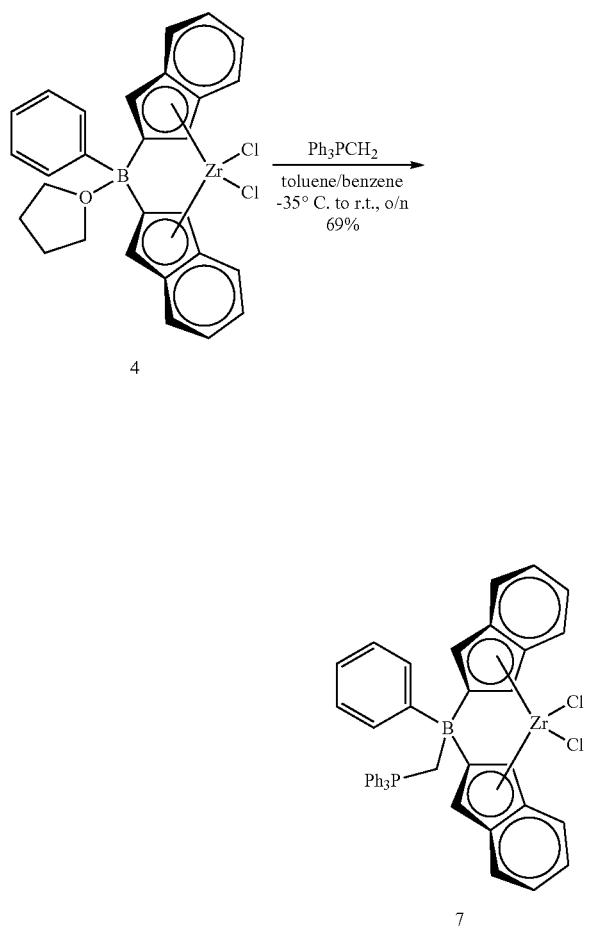

Preparation of Ph₃PCH₂: To a stirred suspension of Ph₃PCH₃Br (3.57 g, 10 mmol) in diethyl ether (40 mL) was added dropwise a solution of PhLi (5.8 mL, 1.8 M in dibutyl ether, 10.44 mmol, 1.05 eq.) at 0° C. The resulting suspension was stirred at 0° C. for half an hour then at room temperature for 3 hours. The orange solution was concentrated in vacuo and the residual brown foam was stirred in hexane (50 mL) at room temperature for overnight. The mixture was filtered and the filter cake was washed with hexane (8 mL×2), dried under high vacuum to give Ph₃PCH₂ (2.4 g, 87%) as a yellow-green powder. The spectra were consistent with the spectra reported in Crimmin, M. R.; White, A. J. P. *Chem. Commun.* 2012, 48, 1745-1747.

To a pre-cooled (−35° C.) suspension of compound 4 (0.18 g, 0.33 mmol) in toluene (9 mL) and benzene (3 mL) was added Ph₃PCH₂ (90 mg, 0.33 mmol, 1.0 eq.) in one portion. The resulting suspension was then stirred at room temperature overnight. The mixture was filtered and the filter cake was washed with hexane (5 mL), dried under high vacuum to provide compound 7 (0.17 g, 69%) as a bright yellow powder. $^{11}$B NMR (128 MHz, CD₂Cl₂) δ −11.8; $^{31}$P NMR (162 MHz, CD₂Cl₂) δ 28.6, 28.5; $^1$H NMR (400 MHz, CD₂Cl₂) δ 7.60-7.85 (3H, m), 7.25-7.56 (21H, m), 6.96-7.08 (4H, m), 5.76-6.03 (4H, m), 2.84 (2H, t, J=17.2 Hz).

Example 9. Synthesis of Compound 8

To the pre-cooled (−35° C.) suspension of compound 2 (0.37 g, 1.12 mmol) in toluene (16 mL) was added TiCl₄(THF)₂ (0.39 g, 1.17 mmol, 1.05 eq.) in one portion. The resulting suspension was then stirred at room temperature for 5 hours.

The mixture was filtered through celite and the residue was washed with methylene chloride (6 mL×2). The combined filtrates were then concentrated. The resulting residue was dissolved in methylene chloride, after which time slow addition of hexanes causes precipitation of the desired complex. The solid was collected by filtration, and the precipitation procedure repeated, to give compound 8 (0.2 g, 35%) as a brown powder. $^{11}$B NMR (128 MHz, CD₂Cl₂) δ 9.1; $^1$H NMR (400 MHz, CD₂Cl₂) δ 7.89 (2H, d, J=6.0 Hz), 7.41-7.50 (7H, m), 7.15-7.24 (4H, m), 6.45 (2H, d, J=1.6 Hz), 5.81 (2H, d, J=1.2 Hz), 4.62 (4H, s), 2.06 (4H, s).

Example 10. Synthesis of Compound 9

-continued

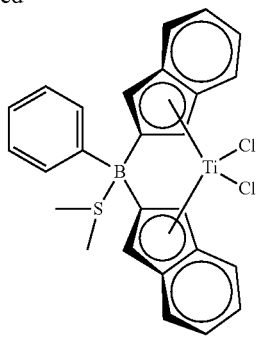

9

In the same manner as 8, Compound 9 was synthesized as a yellow powder (0.16 g, 27%) from compound 2 (0.4 g, 1.21 mmol) and TiCl$_4$(Me$_2$S)$_2$ (0.4 g, 1.27 mmol, 1.05 eq.) in toluene (16 mL). $^{11}$B NMR (128 MHz, CD$_2$Cl$_2$) δ −1.3; $^1$H NMR (400 MHz, CD$_2$Cl$_2$) δ 7.76 (2H, d, J=5.6 Hz), 7.43-7.50 (7H, m), 7.18-7.22 (4H, m), 6.48 (2H, s), 5.98 (2H, s), 2.22 (6H, s).

Example 11. Synthesis of Compound 10

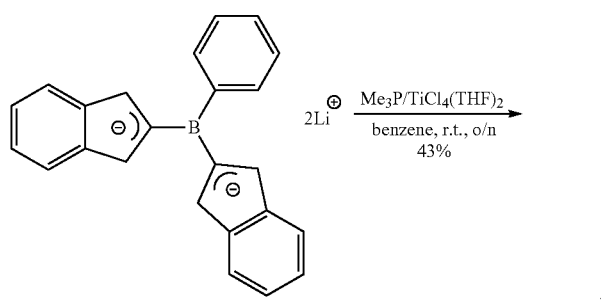

2

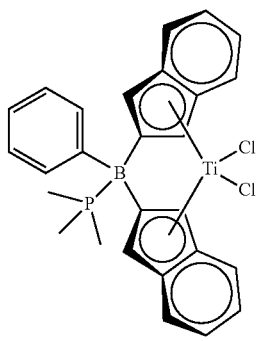

10

To a stirred suspension of compound 2 (0.3 g, 0.91 mmol) in benzene (10 mL) was added trimethylphosphine (7.3 mL, 1.0M in toluene, 7.3 mmol, 8.0 eq.) at room temperature. The resulting red brown suspension was stirred at room temperature for 30 minutes before TiCl$_4$(THF)$_2$ (0.32 g, 0.96 mmol, 1.05 eq.) was added in one portion at room temperature. After the suspension was stirred at room temperature for 5 hours, it was filtered through celite and the residue was washed with methylene chloride (6 mL×2). The combined filtrates were then concentrated. The resulting residue was dissolved in methylene chloride, after which time slow addition of hexanes causes precipitation of the desired complex. The solid was collected by filtration, and the precipitation procedure repeated, to give compound 10 (0.2 g, 43%) as a brown powder. $^{11}$B NMR (128 MHz, CD$_2$Cl$_2$) δ −11.9 (m); $^{31}$P NMR (162 MHz, CD$_2$Cl$_2$) δ −15.4 (m); $^1$H NMR (400 MHz, CD$_2$Cl$_2$) δ 7.74 (2H, d, J=5.6 Hz), 7.36-7.44 (7H, m), 7.14-7.21 (4H, m), 6.26 (2H, s), 6.08 (2H, s), 1.58 (9H, d, J=10.8 Hz).

Example 12. Synthesis of Compound 11

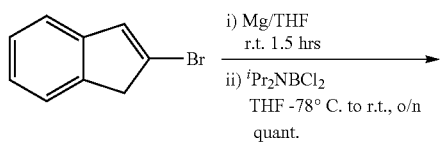

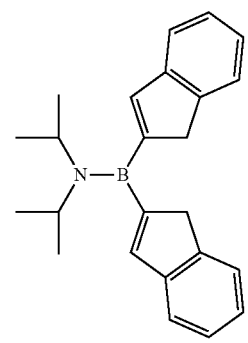

11

A Schlenk flask was charged with a magnetic stir bar and Mg turnings (264 mg, 11 mmol, 6.7 eq.) and flame-dried under vacuum. After cooling, the flask was purged to N$_2$, anhydrous THF (3 mL) was added to just cover the turnings, and stirring was commenced. Several drops of 1,2-dibromoethane was added as initiator, and a heat gun used to briefly reflux the contents, after which the flask was placed in a 25° C. water bath. In a separate flame-dried flask under N$_2$ atmosphere, 2-bromoindene (715 mg, 3.67 mmol, 2.2 eq.) was dissolved in 10 mL anhydrous THF. A cannula was then used to transfer this solution onto the activated magnesium turnings over 5 min, resulting in a red, opaque solution. After 1.5 h, a separate flame-dried flask under N$_2$ atmosphere was charged with $^i$Pr$_2$NBCl$_2$ (0.3 g, 1.65 mmol, 1.0 eq.) in 10 mL anhydrous THF and cooled to −78° C. To this was added, by cannula, the Grignard solution over 10 min., and the reaction flask was brought to ambient temperature for overnight. The pale orange solution was concentrated and the residue was dissolved in CH$_2$Cl$_2$ (30 mL). The suspension was filtered through celite and the filtrate was concentrated to provide compound 11 (0.56 g, quant.) as a yellow powder. $^{11}$B NMR (128 MHz, CD$_2$Cl$_2$) δ 40.4; $^1$H-NMR (400 MHz, CD$_2$Cl$_2$) 7.37 (2H, d, J=7.6 Hz), 7.33 (2H, d, J=7.6 Hz), 7.19 (2H, t, J=7.6 Hz), 7.06 (2H, td, J=7.6, 1.2 Hz), 6.81 (2H, s), 3.85 (2H, m), 3.38 (4H, s), 1.25 (12H, d, J=6.8 Hz).

Example 13. Synthesis of Compound 12

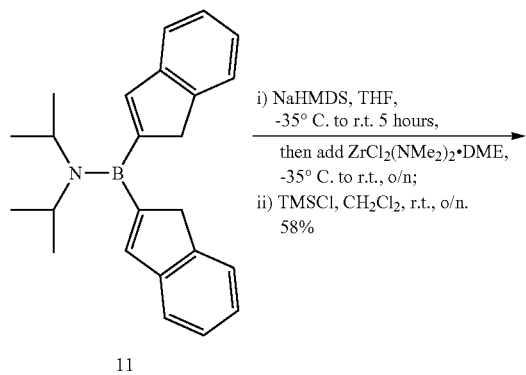

11

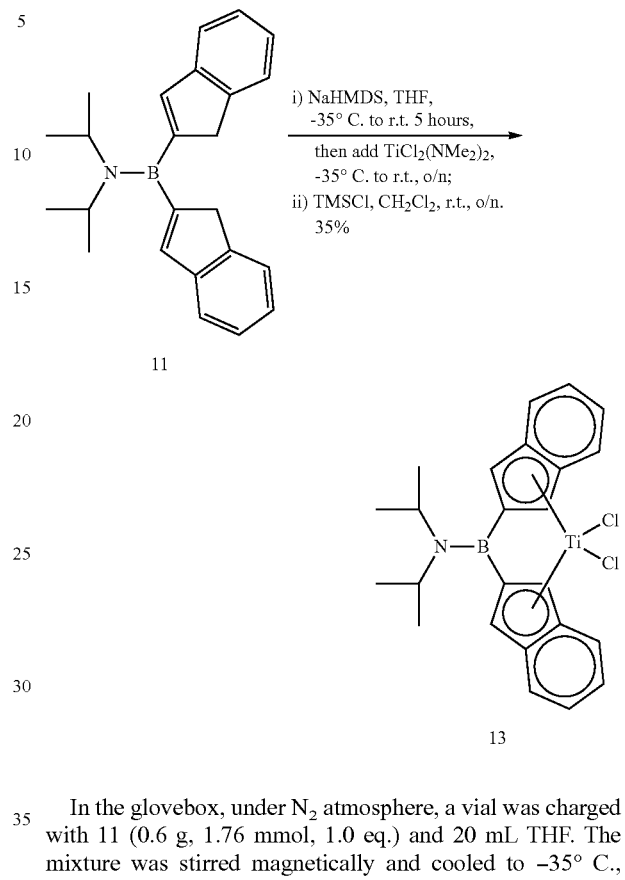

12

In the glovebox, under $N_2$ atmosphere, a vial was charged with 11 (0.6 g, 1.76 mmol, 1.0 eq.) and 20 mL THF. The mixture was stirred magnetically and cooled to −35° C., after which time solid NaHMDS (0.71 g, 3.87 mmol, 2.2 eq.) was added in one portion. The reaction was allowed to warm slowly to ambient temperature and stirred for a total time of 5 h. The homogenous solution was then cooled back to −35° C. and solid $(Me_2N)_2ZrCl_2 \cdot DME$ (0.69 g, 1.86 mmol, 1.05 eq.) was added. The reaction mixture was allowed to warm slowly to ambient temperature and stirred overnight. After this time, the THF was removed in vacuo. The residue was filtered through Celite with PhH and concentrated. The resultant residue was dissolved in 20 mL $CH_2Cl_2$, after which $Me_3SiCl$ (0.67 mL, 5.28 mmol, 3.0 eq.) was added. The reaction mixture was stirred magnetically for overnight. There were some precipitates in the mixture, which was collected by filtration, washed with $CH_2Cl_2$ (3 mL) and dried in vacuo to give compound 12 (130 mg, 15%) as a yellow powder. The combined filtrates were concentrated and the resulting residue was dissolved in $CH_2Cl_2$, after which time slow addition of pentanes causes precipitation of 12. The supernatant was decanted, and the procedure repeated, to give the $2^{nd}$ batch of 12 (380 mg, 43%) as a yellow powder. $^{11}B$ NMR (128 MHz, $CD_2Cl_2$) δ 38.8; $^1H$-NMR (400 MHz, $CD_2Cl_2$) 7.54 (2H, d, J=6.4 Hz), 7.53 (2H, d, J=6.4 Hz), 7.20 (2H, d, J=6.4 Hz), 7.19 (2H, d, J=6.4 Hz), 6.06 (4H, s), 4.00 (2H, m), 1.41 (12H, d, J=6.8 Hz); $^{13}C$-NMR (100 MHz, $CD_2Cl_2$) 131.90, 126.01, 125.15, 104.03, 50.08, 24.60.

Example 14. Synthesis of Compound 13

In the glovebox, under $N_2$ atmosphere, a vial was charged with 11 (0.6 g, 1.76 mmol, 1.0 eq.) and 20 mL THF. The mixture was stirred magnetically and cooled to −35° C., after which time solid NaHMDS (0.71 g, 3.87 mmol, 2.2 eq.) was added in one portion. The reaction was allowed to warm slowly to ambient temperature and stirred for a total time of 5 h. The homogenous solution was then cooled back to −35° C. and solid $(Me_2N)_2TiCl_2$ (0.44 g, 1.86 mmol, 1.05 eq.) was added. The reaction mixture was allowed to warm slowly to ambient temperature and stirred overnight. After this time, the THF was removed in vacuo. The residue was filtered through Celite with PhH and concentrated. The residue was taken up in 20 mL $CH_2Cl_2$, after which trimethylsilylchloride (0.67 mL, 5.28 mmol, 3.0 eq.) was added. The reaction mixture was stirred magnetically for overnight, then the volatiles were removed in vacuo. The residue was dissolved in $CH_2Cl_2$, and slow addition of excess pentanes causes precipitation of desired complex, which was collected by filtration, washed with pentane and dried in vacuo to give compound 13 (265 mg, 33%) as a brown powder. $^{11}B$ NMR (128 MHz, $CD_2Cl_2$) δ 38.7; $^1H$-NMR (400 MHz, $CD_2Cl_2$) δ 7.50 (2H, d, J=6.4 Hz), 7.49 (2H, d, J=6.4 Hz), 7.26 (2H, d, J=6.4 Hz), 7.25 (2H, d, J=6.4 Hz), 6.17 (4H, s), 4.00 (2H, m), 1.42 (12H, d, J=6.8 Hz); $^{13}C$-NMR (100 MHz, $CD_2Cl_2$) δ 136.31, 127.31, 125.79, 111.60, 50.26, 24.66.

Examples 15 to 24 Ethylene Polymerization

Around 1 mg of a compound 3-13 was suspended in 5 ml toluene. Methylalumoxane (10% in toluene, M:Al=1:1000) was added to the suspended compound in toluene. After around two minutes of shaking, the mixture was transferred under inert atmosphere to a 2 liter autoclave reactor filled with 250 ml of iso-pentane and 100 ml of 1-hexene. The reactor was thermostated at 60° C. An ethylene pressure of 20 bar was applied for 1 hour. After releasing the pressure, the polymer was filtered through an airless filter funnel, washed with diluted hydrochloric acid, water and acetone, and finally dried in vacuum. The polymerization results are presented in Table 1.

TABLE 1

The ethylene polymerization activities and GPC results of the polyethylenes produced by compounds 3-13.

| Example | Compound Number | Productivity (g PE/g Cat) | Mn (g/mol) | MW (g/mol) | MWD |
|---|---|---|---|---|---|
| 15 | 3 | 127500 | 15098 | 143218 | 9.49 |
| 16 | 4 | 10000 | 19245 | 414185 | 21.52 |
| 17 | 5 | 163500 | 2650 | 10000 | 3.77 |
| 18 | 6 | 40000 | 6549 | 19405 | 2.96 |
| 19 | 7 | 35000 | 12792 | 30911 | 2.42 |
| 20 | 8 | 500 | 99431 | 386172 | 3.88 |
| 21 | 9 | 500 | 51402 | 328063 | 6.38 |
| 22 | 10 | 3750 | 84753 | 391080 | 4.61 |
| 23 | 12 | 20500 | 8807 | 22370 | 2.54 |
| 24 | 13 | 2220 | 16962 | 73106 | 4.31 |

The GPC results of polyethylenes produced with these catalysts displayed broad and narrow molecular weight distributions. These results can be assigned to the generation of different active sites during activation by methylaluminoxane (MAO). The GPC spectra of polyethylenes produced by compounds 3 and 4 are shown (see FIG. 1).

The invention claimed is:

1. A metallocene complex selected from the group consisting of 2-indenyl complexes I, II, III and IV,

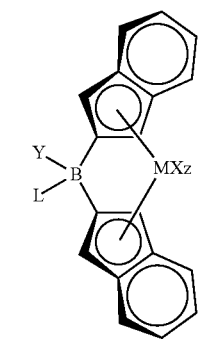
(I)

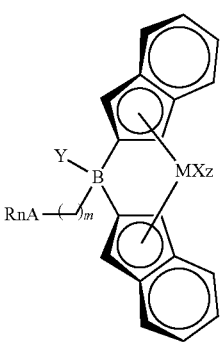
(II)

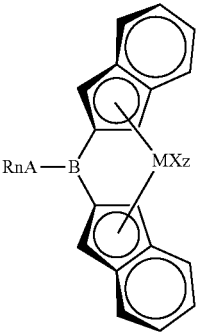
(III)

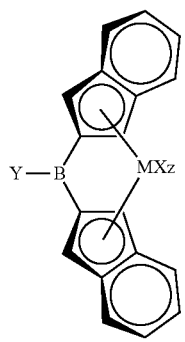
(IV)

wherein
Y is a $C_1$-$C_{20}$ linear, branched or cyclic hydrocarbyl group, or a $C_6$-$C_{30}$ aryl or substituted aryl group;
L is an electron-donating ligand;
A is an element selected from Group 15 or 16 of the Periodic System of the Elements;
R is a $C_1$-$C_{30}$ alkyl, aryl, or substituted aryl group;
n is the number of R groups and is an integer from 1 to 3;
m is the number of carbon atoms in the hydrocarbyl group between A and B and is an integer from 1 to 4;
B is a boron atom;
M is a metal selected from lanthanides or transition metals from group 3, 4, 5 or 6 of the Periodic System of the Elements;
X is an anionic ligand to M; and
z is the number of X groups and equals the valence of M minus 2.

2. The metallocene complex according to claim 1, wherein the metal M is selected from the group consisting of Ti, Zr, Hf, V and Sm, and wherein X is selected from the group consisting of halogen (F, Cl, Br and I), a $C_1$-$C_{20}$ hydrocarbyl group or a $C_1$-$C_{20}$ alkoxy group.

3. The metallocene complex according to claim 1, wherein A is O, S, N or P.

4. The metallocene complex according to claim 1, wherein Y is a $C_6$-$C_{30}$ aryl or substituted aryl group.

5. The metallocene complex according to claim 1, wherein L is selected from pyridine, tetrahydrofuran, dimethylsulfide and trimethylphosphine.

6. The metallocene complex according to claim 5, wherein
Y is a phenyl group;
A is O, S, N or P;

R is a $C_1$-$C_{30}$ alkyl, aryl, or substituted aryl group and n is the number of R groups and is an integer from 1 to 3;

B is a boron atom;

M is selected from the group consisting of Ti, Zr and Hf;

X is Cl or a methyl group; and z is the number of X groups and equals the valence of M minus 2.

7. The metallocene complex according to claim 1, wherein the metallocene complex is immobilized on a support.

8. A catalyst comprising a metallocene complex according to claim 1, and a cocatalyst.

9. A process for the preparation of olefin polymers the process comprising polymerizing one or more olefins in the presence of the metallocene complex according to claim 1 and a cocatalyst.

10. To process according to claim 9, wherein a mixture of ethylene and at least one other olefin of 3 or more carbon atoms is used.

11. The catalyst according to claim 8, wherein

Y is a phenyl group;

A is O, S, N or P;

R is a $C_1$-$C_{30}$ alkyl, aryl, or substituted aryl group and n is the number of R groups and is an integer from 1 to 3;

B is a boron atom;

M is selected from the group consisting of Ti, Zr and Hf;

X is Cl or a methyl group; and z is the number of X groups and equals the valence of M minus 2.

12. The process of claim 9, wherein

Y is a phenyl group;

A is O, S, N or P;

R is a $C_1$-$C_{30}$ alkyl, aryl, or substituted aryl group and n is the number of R groups and is an integer from 1 to 3;

B is a boron atom;

M is selected from the group consisting of Ti, Zr and Hf;

X is Cl or a methyl group; and z is the number of X groups and equals the valence of M minus 2.

13. The process of claim 9, wherein the at least one olefin is ethylene.

\* \* \* \* \*